United States Patent [19]

Hagerman et al.

[11] 4,287,183

[45] Sep. 1, 1981

[54] METHOD OF KILLING RODENTS

[76] Inventors: John D. Hagerman; Brenda M. Hagerman, both of 1641 Lancing Dr., Apt. # 269, Salem, Va. 24153

[21] Appl. No.: 91,653

[22] Filed: Nov. 5, 1979

[51] Int. Cl.$^3$ ............................................. A61K 33/08
[52] U.S. Cl. ...................................... 424/157; 424/84
[58] Field of Search ................................. 424/157, 84

[56] References Cited

PUBLICATIONS

Chem. Abstr. 17: 1701$^2$ (1923).
Chem. Abstr. 20: 2737$^1$ (1926).
Chem. Abstr. 51: 18542d (1957).
Chem. Abstr. 52: 15872b (1958).

Primary Examiner—Frank Cacciapaglia, Jr.
Attorney, Agent, or Firm—Norman B. Rainer

[57] ABSTRACT

A rodenticide composition is provided comprising a dry mixture of a first ingredient which is a substance that rodents are fond of eating, and a second ingredient which has the propensity to react with water and thereby transform to a hydrated cementitious solid aggregate. Each of said ingredients is present to the extent of between about 20% and 60% by volume of said composition.

A method of killing rodents is provided comprising disposing quantities of said composition in a manner to avoid contact with water in locations frequented by rodents, and allowing said rodents to ingest effective amounts of said composition.

2 Claims, No Drawings

4,287,183

METHOD OF KILLING RODENTS

BACKGROUND OF THE INVENTION

This invention relates to a composition of matter useful as a rodenticide and to a method for exterminating rodents involving the use of said composition of matter.

Compositions referred to as rodenticides, useful in killing rodents are well known and widely used. Such compositions generally contain at least one substance which rodents are fond of eating and a compound mixed therewith which functions as a poison for the rodent. Many of the poison compounds utilized however are hazardous to persons handling the rodenticide and hazardous to children who might unwarily ingest quantities of the composition. If improperly used, rodenticides may come into contact either directly or indirectly with food products intended for human consumption, whereby posionous compounds in said rodenticides could cause serious illness.

It is accordingly an object of the present invention to provide a rodenticide composition which is substantially innocuous to humans.

It is further object to provide a method for killing rodents by causing said rodents to ingest quantities of said rodenticide composition.

These objects and other objects and advantages of the invention will be apparent from the following description.

SUMMARY OF THE INVENTION

The above and other beneficial objects and advantages are accomplished in accordance with one aspect of the present invention by the provision of a composition comprising a dry mixture of a first ingredient which is a substance that rodents are fond of eating, and a second ingredient which has the propensity to react with liquid phase water and thereby transform to a solid aggregate. The process aspect of this invention involves the placement of a quantity of said composition in powder or pelleted form in a location frequented by rodents, and allowing said rodents to ingest an effective amount of said composition.

DESCRIPTION OF THE PREFERRED EMBODIMENTS

The composition of this invention is produced by preparing a substantially dry homogeneous mixture comprising a first ingredient and a second ingredient, as will hereinafter be defined. In some embodiments, the composition may be converted to a pelletized composition by subjecting the mixture to a conventional pelletizing or tableting operation which generally involves compacting techniques. The term "pelleted composition" as used herein is intended to denote a collection of shaped solid pellets of substantially uniform size, the size of each said pellets being such that the greatest linear dimension is generally between about 0.1 inch and 0.5 inch. The pellets may have the shape of cylindrical or prismatic extrudate rods, spheres, wafers, arcuate and toroidal forms, and still other configurations.

The pelleted state may be formed entirely by means of compressive forces acting upon the dry mixture of ingredients. Alternatively, substances having no adverse affect on the functionality of the composition, and which impart a binding effect, may be incorporated into the mixture to facilitate production of pellets. The crush strength of the pellets is preferably between about 2 pounds and 15 pounds. Pellets having a crush strength below about 2 pounds generally break apart in the course of normal packaging, transportation and handling. Pellets having a crush strength greater than about 15 pounds are less readily consumed by the rodents for whom they are intended.

The pellets may be provided with a coating intended to protect the composition from contact with water, or to maintain the integrity of the pellet, or to achieve still other advantages.

Said first ingredient of the composition of this inventiion is a water-insoluble solid material comprised of carbohydrate, protein or fat substances preferably of nautural origin and which attracts rodents because of its comestible nature. Specific substances suitable for use as said first ingredient include cornmeal, flours derived from various grain products, starches derived from various plant sources, pectins, fishmeal, proteins insolated from soybeans and animal sources, and saturated and unsaturated fats derived from animal and vegetable sources. Preferred species of said first ingredient are those possessing sufficiently low hygroscopicity as to be non-caking upon exposure to moisture and amenable to comminution to a powder form wherein such powders will pass a 100 mesh sieve screen (U.S. Bureau of Standards, Standard Screen Series, 1919) and preferably will pass a 325 mesh screen.

The second ingredient of the composition of this invention is a cementitious powder capable of undergoing a hydration reaction with liquid phase water with attendant change in miscroscopic crystal structure causing cohesive or adhesive bonding of the powder particles to adjacent particles. The bonding action is strong enough to cause formation of integral aggregate structures. The rate at which bonding ensues following contact with liquid phase water is such that significant bonding or structural formation occurs within about 24 hours, and preferably within 12 hours.

Said second ingredient will generally be a water-insoluble inorganic substance in the form of a powder having a size small enough to pass through a 200 mesh screen and preferably pass through a 325 mesh screen. Specific substances suitable for use as the second ingredient include Portland cement, calcium sulfate hemihydrate (generally referred to as Plaster of Paris), and anhydrous calcium oxide. Portland cement is the most preferred second ingredient, particularly a species known as ASTM designation type III high early strength. The high early strength cement, primarily by virtue of its finer particle size, develops a hydrated cementitious structure faster than ordinary Portland cements. In some embodiments of the composition of this invention, two or more cementitious powders may be utilized as the second ingredient.

In preparing the composition of this invention, measured amounts of the two essential components are brought together and intermixed preferably by tumbling in a confining vessel to secure a visibly homogeneous mixture. Because each ingredient is a dry free-flowing solid, and because the relative numbers of particles of each ingredient appears to be more significant than their weight ratio, quantitative measurement of each ingredient is most readily done on a volume basis. The preferred composition of the present invention is comprised of between 20% and 60% by volume of each of the two ingredients. Other components such as dyestuffs, odorants, flow improving agents, tableting aids and desiccants may also be incorporated into the composition.

Although the exact mode of function of the rodenticide composition of this invention is not clearly understood, it is felt that said second ingredient, when ingested by a rodent, provides the dual effect of dehydrating the animal and forming large agglomerate structures which obstruct the digestive system.

The following examples illustrate preferred embodiments of this invention and are not intended to limit the invention in any manner.

EXAMPLE 1

A composition was prepared comprising two parts by volume high-early Portland cement, two parts by volume of plaster of paris, and one part by volume of cornmeal. The composition was thoroughly homogenized by tumble-mixing.

One ounce quantities of said composition was placed in the cages of three albino rats, each rat weighing approximately six ounces. A supply of water was also made available to each rat.

Following the first day of feeding, the stool excreted by each rat was normal. On the second day, there was very little stool, and its texture was extremely hard. By the third day, there was no stool excretion and the rats were dead. The average amount of the composition consumed by each rat was 1/3 ounce.

EXAMPLE 2

One ounce quantities of the composition of Example 1 in the form of ⅛" long cylindrical pellets having a crush strength of 2 pounds, were protectively placed inside eight inch lengths of 4" I.D. tubing. The lengths of tubing were placed in horizontal disposition at ground level locations about a barn known to be infested with rats, said locations being protected from direct contact with water.

Within three weeks following placement of the composition, diminution of the quantities of composition in each container was observed. Also observed was the presence of dead rats and absence of live rats.

While particular examples of the present invention have been shown and described, it is apparent that changes and modifications may be therein without departing from the invention in its broadest aspects. The aim of the appended claims, therefore, is to cover all such changes and modifications as fall within the true spitit and scope of the invention.

Having thus described our invention, what is claimed is:

1. A process for exterminating rodents comprising placing in locations frequented by rodents a rodenticide composition comprised of a substantially dry homogeneous mixture of a first ingredient comprising a carbohydrate, protein, or fat, said first ingredient being a water insoluble comestible solid of natural origin and in the form of a powder capable of passing through a 100 mesh sieve, and a second ingredient comprising a water-insoluble inorganic cementitious powder selected from the group consisting of Portland cement, plaster of paris and calcium oxide, said second ingredient being capable of passing through a 200 mesh screen and capable of reacting with water to undergo hydration with attendant formation of a coherent aggregate structure, said first and second ingredients comprising between about 20% and 60% by volume of said composition.

2. The process of claim 1 wherein the composition is in the form of shaped pellets having an average size between 0.1 and 0.5 inch and a crush strength between about 2 and 15 pounds.

* * * * *